United States Patent [19]

Holland et al.

[11] Patent Number: 4,931,470

[45] Date of Patent: Jun. 5, 1990

[54] ANTIARRHYTHMIC METHOD

[75] Inventors: Donald R. Holland, Indianapolis; David W. Robertson, Greenwood, both of Ind.

[73] Assignee: Eli Lilly and Company, Indianapolis, Ind.

[21] Appl. No.: 290,675

[22] Filed: Dec. 27, 1988

[51] Int. Cl.$^5$ ............................................. A61K 31/165
[52] U.S. Cl. ..................................... 514/619; 514/620
[58] Field of Search ................................. 514/619, 620

[56] References Cited

U.S. PATENT DOCUMENTS

| | | | |
|---|---|---|---|
| 4,004,029 | 1/1977 | Collins et al. | 424/325 |
| 4,638,014 | 1/1987 | Clark | 514/619 |
| 4,684,748 | 8/1987 | Robertson | 514/619 |

OTHER PUBLICATIONS

Robertson et al., *J. Med. Chem.*, 30, 1742 (1987).
Clark et al., *J. Med. Chem.*, 29, 1534 (1986).
Clark et al., *J. Pharm. Sciences*, 76 (1), 18 (1987).
Grammaticakis, *C. R. Acad. Sc. Paris*, 259, 4295 (1964).

*Primary Examiner*—Frederick E. Waddell
*Attorney, Agent, or Firm*—Robert A. Conrad; Leroy Whitaker

[57] ABSTRACT

This invention provides a method of treating or preventing cardiac arrhythmias employing certain 4-amino-N-2,6-(dimethylphenyl)benzamide derivatives.

4 Claims, No Drawings

ANTIARRHYTHMIC METHOD

BACKGROUND

Cardiovascular disorders are the cause of thousands of deaths each year. Cardiac arrhythmias are among such disorders. Arrhythmias are cardiac abnormalities characterized by irregular beating of the heart. Typical arrhythmias include ventricular fibrillation (VF), ventricular tachycardia, auricular flutter, and auricular fibrillation.

A number of drugs are known which display varying degrees of antiarrhythmic activity. Quinidine, procainamide, lidocaine, and digitalis are perhaps the most widely used antiarrhythmic agents. Recent research has developed improved antiarrhythmic agents such as flecainide, bretylium, certain diphenylbutanolamines, and certain 9,9-disubstituted fluorenes; see, e.g., U.S. Pat. No. 4,197,313.

Although it is not generally the case, some antiepileptic drugs, such as phenytoin, also have antiarrhythmic properties. This invention provides a method for treating cardiac arrhythmias employing certain known anticonvulsants of the aminobenzamide class.

SUMMARY OF THE INVENTION

This invention provides a method of treating cardiac arrhythmias comprising administering to a mammal suffering from an arrhythmia and in need of treatment or to a mammal suspected of developing a cardiac arrhythmia an antiarrhythmic amount of an aminobenzamide of the formula

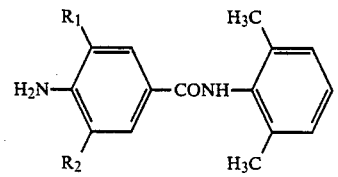

wherein $R_1$ and $R_2$ are each independently hydrogen or methyl, or a pharmaceutically acceptable acid addition salt thereof.

DETAILED DESCRIPTION OF THE INVENTION

The three compounds represented by Formula I are 4-amino-N-(2,6-dimethylphenyl)benzamide, 4-amino-N-(2,6-dimethylphenyl)-3-methylbenzamide, and 4-amino-N-(2,6-dimethylphenyl)-3,5-dimethylbenzamide. The former compound is preferred and has been reported in the literature by the designation LY201116 as an anticonvulsant agent. These three compounds are described in the art; see, e.g., U.S. Pat. Nos. 4,684,748, 4,638,014, generically described in U.S. Pat. No. 4,004,029, and also described in *J. Med. Chem.*, 30, 1742 (1987), all of which are expressly incorporated within this specification by reference. Included within the respective references is a description of the pharmaceutically acceptable acid addition salts of each of the three compounds. The preferred salts are those derived from inorganic acids, especially hydrochloric acid.

According to this invention, a compound of Formula I, or a pharmaceutically acceptable salt thereof, is administered orally or parenterally to a mammal suffering from an arrhythmia in need of therapeutic treatment, or to a mammal suspected of developing an arrhythmia and in need of prophylactic treatment. The effectiveness of the compounds in such treatment has been determined by evaluating a compound of the above formula in biological assays designed to measure antiarrhythmic activity in mammals. One such assay comprises administering a compound of unknown biological activity to a dog suffering from an experimentally induced cardiac arrhythmia, and observing whether or not the compound effects conversion of the arrhythmia to a normal sinus rhythm, and if so, for how long the conversion persists.

LY201116 converted the ventricular arrhythmias elicited by ouabain to sinus rhythm. Male beagle dogs (8.3–12.8 kg) were anesthetized with sodium pentobarbital (35 mg/kg, i.v.) and respired through a cuffed endotracheal tube using a positive pressure respirator (18 strokes/min, 20 ml/kg/stroke). Body temperature was maintained at 37–38° C. using a water heated pad. Lead II ECG was obtained using subdermal needle electrodes and a strip-chart recorder. Infusion cannulas were placed in each cephalic vein: one for administration of ouabain and test compound and the second for infusion of pentobarbital maintenance dose (0.05–0.1 mg/kg/min).

Arrhythmias were elicited with ouabain administered i.v. according to the following schedule: An initial dose of 50 μg/kg was followed 15 minutes later by 10 μg/kg. Additional doses of ouabain at 5 μg/kg were given, if necessary, every 15 minutes until ventricular arrhythmias appeared. If less than 50% ventricular beats were present or if arrhythmias did not persist for 30 minutes, an additional 2.5 μg/kg of ouabain was injected. Following 30 minutes of continuous arrhythmias, test compounds were given by continuous i.v. infusion until arrhythmias reverted to 100% sinus beats. Infusion of the test compound was continued to twice the converting dose and ECG was followed for two hours thereafter to observe whether the antiarrhythmic effect was sustained. Dogs were allowed to recover and returned to their pens. The results of testing LY201116 (4-amino-N-(2,6-dimethylphenyl)benzamide) and phenytoin are reported in Table 1.

TABLE 1

| OUABAIN CONVERTING DOSES IN ANESTHETIZED BEAGLES | | | | | |
|---|---|---|---|---|---|
| COMPOUND | INFUSION RATE (μg/kg/min) | OUABAIN DOSE (μg/kg) | CONVERTING DOSE (mg/kg) | n | MEAN DURATION (min) |
| LY201116 | 100 | 63.8 ± 1.6 | 3.7 ± 1.0 | 4 | >120 |
| LY201116 | 200 | 66.9 ± 2.6 | 4.4 ± 1.4 | 4 | >90 |
| Phenytoin | 500 | 63.8 ± 1.6 | 12.4 ± 3.9 | 4 | >120 |

Values in table are means ± standard errors. The same four dogs were used throughout. In treatment group LY201116 (100 μg/kg/min), duration was not determined in one animal and, hence, the >120 min value was obtained from three animals.

Compound LY201116 was also evaluated for its effect upon electrophysiology in canine Purkinje fibers according to the procedures of Steinberg and Wiest, *J. Cardiovascular Pharmacology*, 6, 614 (1984). Table II reports pretreatment control values and effects produced by LY201116 at doses of $10^{-6}$ to $10^{-4}$ M. The following abbreviations are used in Table II:

AMP—Action potential amplitude;
$APD_{50}$—Action potential duration at 50% repolarization;
$APD_{95}$—Action potential duration at 95% repolarization;
RP—Resting membrane potential;
$S_1$—Upstroke velocity of action potential stimulated at 1 Hz
$S_2$—Upstroke velocity of action potential elicited immediately after repolarization.
$S_{\frac{1}{2}}$—The ratio of $S_1$ to $S_2$.
CT—Conduction time from stimulus artefact to upstroke of action potential.

TABLE 2

ELECTROPHYSIOLOGY OF LY201116 IN CANINE PURKINJE FIBER

| | CONT. | 1E-6M | 3E-6M | 1E-5M | 1E-4M |
|---|---|---|---|---|---|
| AMP(mV) | 123 ± .6 | 123 ± .7 | 121 ± 1 | 123 ± .7 | 120 ± 1 |
| $APD_{50}$(msec) | 202 ± 6 | 189 ± 7* | 183 ± 6* | 155 ± 4* | 105 ± 12* |
| $APD_{95}$(msec) | 312 ± 8 | 296 ± 7* | 288 ± 7* | 265 ± 5* | 232 ± 6* |
| RP(mV) | 88.2 ± .3 | 88.7 ± .2 | 87.8 ± .6 | 89.1 ± .1 | 87.1 ± .7 |
| $S_1$(V/sec) | 453 ± 39 | 456 ± 51 | 425 ± 35 | 442 ± 32* | 354 ± 52* |
| $S_2$(V/sec) | 453 ± 40 | 453 ± 51 | 425 ± 35 | 416 ± 34* | 256 ± 48* |
| $S_1/S_2$ | 1 ± 0 | 1 ± .01 | 1 ± 0 | 1.1 ± .02* | 1.5 ± .12* |
| CT(msec) | 4.1 ± .7 | 3.4 ± .6 | 4.6 ± .7 | 5.1 ± .7* | 6.6 ± 1.2* |

*$p \leq .05$, compared to control (Student's paired t test).

As shown in Table 2, LY201116 decreased action potential duration, decreased upstroke velocity of the action potential elicited at 1 Hz and the action potential immediately after repolarization and increased conduction time.

Finally, in dogs anesthetized with pentobarbital, LY201116 produced cardiovascular effects consistent with an antiarrhythmic action of the drug. Twelve beagle dogs of either sex and weighing 8-13 kg were anesthetized with pentobarbital sodium by bolus injection of 35 mg/kg followed by constant infusion of 6 mg/kg/hour. Animals were ventilated (18 strokes/min and 20 ml/kg/stroke) through a cuffed endotracheal tube and body temperature was maintained at 37-39° C. using a water heated pad. Lead II ECG was obtained using subdermal needle electrodes and a strip-chart recorder and the PR interval was measured from the tracings. Femoral artery blood pressure was measured through a heparin-filled cannula using a Statham P23Db pressure transducer and the strip-chart recorder. The signal was digitalized and the mean pressure was determined by computer from the area under the curve of the pulsatile pressure v. time. Left ventricular pressure was measured through a heparin-filled cannula inserted through the carotid artery using a Statham P23Db pressure transducer and strip-chart recorder. The rate of increase in left ventricular pressure at 60 mm Hg ($dP/dt_{60}$) was determined by computer from the digitalized signal. A Swan-Ganz catheter was inserted through the femoral vein, inferior vena cava and right heart and into the pulmonary artery. Cardiac output was measured by the thermal dilution method using the Swan-Ganz catheter and a cardiac output computer.

Four dogs received LY201116, four dogs received phenytoin, and four dogs received vehicle by bolus i.v. injection over 2 min. Measurements were taken prior to drug or vehicle treatment and 2 min after the end of dose injection and the percent changes were calculated.

Results in Table 3 show effects of 10 mg/kg doses of either LY201116 or phenytoin and corresponding effects of vehicle in absence of any drug. LY201116 produced negative dromotropy (increase in PR interval), negative inotropy (decrease in $dP/dt_{60}$ and cardiac output) and negative chronotropy, effects that are consistent with antiarrhythmic action of LY201116.

TABLE 3

CARDIOVASCULAR EFFECTS OF LY201116 IN PENTOBARBITAL ANESTHETIZED DOGS

| Treatment | PR Interval (msec) | LV $dP/dt_{60}$ (mmHg/sec) | Cardiac Output (1/min) | Mean Arterial Blood Pressure (mmHg) | Heart Rate Beats/min |
|---|---|---|---|---|---|
| Vehicle | | | | | |
| Pre-treatment | 95 ± 3 | 2450 ± 180 | 1.2 ± 0.2 | 124 ± 7 | 140 ± 11 |
| Percent Change | 10.3 ± 3.3 | −4 ± 17 | 10 ± 16 | −2 ± 6 | −12 ± 1 |
| LY201116 (10 mg/kg) | | | | | |
| Pre-treatment | 81 ± 1 | 2171 ± 97 | 1.0 ± 0.1 | 124 ± 6 | 148 ± 6 |
| Percent Change | 44.0 ± 3.0* | −71 ± 11* | −30 ± 11 | −41 ± 8* | −21 ± 1* |
| Phenytoin (10 mg/kg) | | | | | |
| Pre-treatment | 77 ± 3 | 3016 ± 340 | 1.4 ± 0.2 | 126 ± 5 | 144 ± 4 |
| Percent Change | 18.0 ± 3.0* | −75 ± 12* | −39 ± 12* | −44 ± 8* | −21 ± 3* |

*Percent change significantly different from value for vehicle group using least significant difference based on analysis of variance (P = 0.05).

According to the method of this invention, the compounds of Formula I are employed in combatting cardiac arrhythmias in mammals by administering an antiarrhythmic amount of the compound of Formula I to a mammal. The compounds are effective as antiarrhythmic agents when administered internally to a mammal so as to introduce the compound into the mammal's cardiovascular system. Parenteral administration of the compounds can be accomplished by intraperitoneal, subcutaneous, or intravenous injection. The compounds alternatively can be administered orally in the form of tablets, capsules, elixirs, syrups, buccal seals, and the like. The compounds of Formula I have good antiarrhythmic activity both therapeutically, for instance, when administered to a mammal suffering from arrhythmia and in need of treatment, and prophylactically when administered to a mammal suspected of developing an arrhythmia, thereby protecting the animal against the occurance or recurrence of arrhythmias.

The compounds of Formula I are generally utilized as pharmaceutical formulations. Such formulations ideally contain from about 1 to about 95% by weight of a compound of Formula I in combination with a suitable pharmaceutical diluent, excipient, or carrier therefor. Diluents commonly utilized in formulating the compounds in solid form suitable for oral administration includes starch, lactose, gelatin, silica gel, rice flour, carboxymethylcellulose, and the like. Carriers employed in liquid formulations suitable for parenteral administration via the intravenous, intramuscular, or subcutaneous routes include water, saline, glucose syrup, ethanol, corn oil, and the like.

The compounds of Formula I can be administered to a mammal suffering from an arrhythmia and in need of treatment, or to a mammal suspected of developing an arrhythmia and in need of prophylactic treatment. Parenteral administration may be preferred for subjects suffering from a life-threatening arrhythmia. Oral administration is preferred for maintenance or prophylactic treatment. The compounds ideally are formulated in such a way that the effective dose of a compound of Formula I is sufficient to treat the arrhythmia. Such doses typically will be from about 0.1 to about 25 mg/kg. A typical oral dose for the treatment of a patient suffering from an arrhythmia and weighing about 70 kg will be, for example, from about 7 to about 400 mg of a suitably formulated benzamide of Formula I, for example, 4-amino-N-(2,6-dimethylphenyl)benzamide. Such oral dosing may be made from one to about four times each day, or as dictated by the particular patient and condition be treated. The compound can, of course, be formulated for parenteral administration, for instance by intravenous infusion. Such formulations can be prepared by dissolving by 500 mg of the compound of Formula I in a suitable diluent such as 1000 ml of 5% glucose. Such solutions can be infused into a patient suffering from an arrhythmia at the rate of about 1 ml/min.

We claim:

1. A method of treating cardiac arrhythmias comprising administering to a mammal suffering from an arrhythmia and in need of treatment an antiarrhythmic amount of a benzamide of the formula

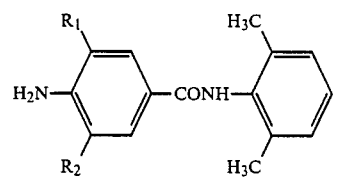

wherein $R_1$ and $R_2$ are each independently hydrogen or methyl, or a pharmaceutically acceptable salt thereof.

2. The method of claim 1 wherein the compound administered is 4-amino-N-(2,6-dimethylphenyl)benzamide or a pharmaceutically acceptable salt thereof.

3. The method of claim 1 wherein the compound administered is 4-amino-N-(2,6-dimethylphenyl)-3-methylbenzamide or a pharmaceutically acceptable salt thereof.

4. The method of claim 1 wherein the compound administered is 4-amino-N-(2,6-dimethylphenyl)-3,5-dimethylbenzamide or a pharmaceutically acceptable salt thereof.

* * * * *